United States Patent [19]
Eder et al.

[11] Patent Number: 5,743,905
[45] Date of Patent: Apr. 28, 1998

[54] PARTIALLY INSULATED OCCLUSION DEVICE

[75] Inventors: Joseph Eder, Los Altos; Guido Guglielmi, Santa Monica; Cheng Ji, Los Angeles, all of Calif.

[73] Assignee: Target Therapeutics, Inc., Fremont, Calif.

[21] Appl. No.: 607,592

[22] Filed: Feb. 27, 1996

Related U.S. Application Data

[63] Continuation of Ser. No. 591,821, Jan. 25, 1996, abandoned, which is a continuation of Ser. No. 499,428, Jul. 7, 1995, abandoned.

[51] Int. Cl.$^6$ .................................................... A61B 17/38
[52] U.S. Cl. ................................................ 606/32; 606/40
[58] Field of Search ........................... 606/32–34, 37–42, 606/45–50; 607/116, 119, 154, 156

[56] References Cited

U.S. PATENT DOCUMENTS

| | | |
|---|---|---|
| 3,174,851 | 3/1965 | Buehler et al. |
| 3,351,463 | 11/1967 | Rozner et al. |

(List continued on next page.)

FOREIGN PATENT DOCUMENTS

| | | |
|---|---|---|
| 0407057 | 1/1991 | European Pat. Off. |

OTHER PUBLICATIONS

U.S. Patent Application Ser. No. 08/499,525 (filed Jul. 7, 1995).
Becker et al. "Long–Term Occlusion of the Porcine Cystic Duct by Means of Endoluminal Radio–Frequency Electrocoagulation" *Radiology* (1988) 167:63–68.
Bubien et al., "What you Need to Know About Radiofrequency Ablation" *AJN* (Jul. 1993) pp. 30–36.
El–Sabban et al., "Stability of Thrombosis Induced by Electrocoagulation of Rat Middle Cerebral Artery" *Stroke* (1994) 25:2241–2245.

Gold et al., "Transarterial Electrocoagulation Therapy of a Pseudoaneurysm in the Head of the Pancreas" *American Journal of Roentgenology* (1975) 125:422–426.
Kopecky et al., "Percutaneous Transrenal Endoureteral Radio–frequency Electrocautery for Occlusion: Case Report" *Radiology* (1989) 170:1047–1048.
Nath et al., "Basic Aspects of Radiofrequency Catheter Ablation" *J. Cardiovascular electrophysiol.* (1994) 5:863–876.
Phillips, "Transcatheter Electrocoagulation of Blood Vessels" *Investigative Radiology* (1973) 8:295–304.
Phillips et al., "Experimental Closure of Arteriovenous Fistula by Transcatheter Electrocoagulation" *Diagnostic Radiology* (1975) 115:319–321.
Rish, "Cerebrovascular Accident After Percutaneous rf Thermocoagulation of the Trigeminal Ganglion" *J. Neurosurg.* (1976) 44:376–377.
Tanigawa et al., "Intraarterial Occlusion by Radiofrequency" *Acta Radiologica* (1994) 35:626–628.
Thompson et al., "Transcatheter Electrocoagulation: A Therapeutic Angiographic Technique for Vessel Occlusion" *Investigative Radiology* (1977) 12:146–153.
Thompson et al., "Vessel Occlusion with Transcatheter Electrocoagulation: Initial Clinical Experience" *Diagnostic Radiology* (1979) 133:335–340.
Bowick, "Impedance Matching" *RF Circuit Design* Howard W. Sams & Co., ISBN 0–672–21868 (1993) pp. 66–67, 104–105, 160–161.

*Primary Examiner*—John P. Lacyk
*Assistant Examiner*—Bryan K. Yarnell
*Attorney, Agent, or Firm*—Morrison & Foerster LLP

[57] ABSTRACT

This is a device used in the occlusion of various lumen and other cavities in the body. In particular, it may be used to form an endovascular occlusion through the application of a radio-frequency modulated voltage to the device after its placement in the body. The elongated device is distally insulated to optimize its occlusive activity without harm to the body.

10 Claims, 4 Drawing Sheets

U.S. PATENT DOCUMENTS

| | | |
|---|---|---|
| 3,675,655 | 7/1972 | Sittner . |
| 3,753,700 | 8/1973 | Harrison et al. . |
| 3,868,956 | 3/1975 | Alfidi et al. . |
| 4,057,063 | 11/1977 | Gieles et al. . |
| 4,416,276 | 11/1983 | Newton et al. . |
| 4,494,539 | 1/1985 | Zenitani et al. . |
| 4,565,200 | 1/1986 | Cosman ................................. 606/50 |
| 4,582,057 | 4/1986 | Auth et al. . |
| 4,700,701 | 10/1987 | Montaldi et al. . |
| 4,739,768 | 4/1988 | Engelson . |
| 4,884,575 | 12/1989 | Sanders . |
| 4,907,589 | 3/1990 | Cosman . |
| 4,974,595 | 12/1990 | Nordenström . |
| 4,994,069 | 2/1991 | Ritchart et al. . |
| 5,057,105 | 10/1991 | Malone et al. . |
| 5,067,491 | 11/1991 | Taylor, III et al. . |
| 5,078,736 | 1/1992 | Behl . |
| 5,122,136 | 6/1992 | Guglielmi et al. . |
| 5,167,658 | 12/1992 | Ensslin . |
| 5,170,802 | 12/1992 | Mehra . |
| 5,174,295 | 12/1992 | Christian et al. . |
| 5,178,618 | 1/1993 | Kandarpa . |
| 5,190,517 | 3/1993 | Zieve et al. . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,300,068 | 4/1994 | Rosar et al. . |
| 5,304,194 | 4/1994 | Chee et al. . |
| 5,304,195 | 4/1994 | Twyford, Jr. et al. . |
| 5,312,415 | 5/1994 | Palermo . |
| 5,341,807 | 8/1994 | Nardella . |
| 5,350,397 | 9/1994 | Palermo et al. . |
| 5,354,295 | 10/1994 | Gulielmi et al. ................... 606/32 |
| 5,372,596 | 12/1994 | Klicek et al. . |
| 5,380,320 | 1/1995 | Morris ................................. 606/32 |
| 5,382,259 | 1/1995 | Phelps et al. . |
| 5,405,322 | 4/1995 | Lennox et al. . |
| 5,411,546 | 5/1995 | Bowald et al. . |
| 5,415,657 | 5/1995 | Taymor-Luria . |
| 5,423,810 | 6/1995 | Goble et al. . |
| 5,423,829 | 6/1995 | Pham et al. . |
| 5,437,664 | 8/1995 | Cohen et al. . |
| 5,496,312 | 3/1996 | Klicek . |
| 5,556,396 | 9/1996 | Cohen et al. . |
| 5,558,671 | 9/1996 | Yates . |
| 5,562,703 | 10/1996 | Desai . |
| 5,569,241 | 10/1996 | Edwards . |
| 5,569,242 | 10/1996 | Lax et al. . |
| 5,569,245 | 10/1996 | Guglielmi et al. . |
| 5,582,609 | 12/1996 | Swanson et al. . |

PARTIALLY INSULATED OCCLUSION DEVICE

RELATED PATENT APPLICATION

This application is a continuation of U.S. Ser. No. 08/591,821 filed Jan. 25, 1996, now abandoned, which is a continuation of U.S. Ser. No. 08/499,428 filed Jul. 7, 1995, now abandoned.

FIELD OF THE INVENTION

This invention is a device used in the occlusion of various lumen or cavities in the body. In particular, it may be used to form an endovascular occlusion through the application of a radio-frequency modulated current to the device after its placement in the body. The elongated device is distally insulated to optimize its occlusive activity without harm to the body.

BACKGROUND OF THE INVENTION

A wide variety of medical procedures are facilitated by occluding such body lumens and cavities as the arteries, veins, vascular aneurysms, various vascular malformations (e.g., AVM's), fallopian tubes, vas deferens, ureters, and the like. For instance, an extravascular approach to treatment of aneurysms involves surgically exposing or stereotaxically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by reference.

A still further approach is the least invasive and is additionally described in Guglielmi et al. It is the endovascular approach. In this approach, the interior of the aneurysm is entered by use of a catheter such as those shown in Engelson (Catheter Guidewire), U.S. Pat. No. 4,884,575 and also in Engelson (Catheter for Guidewire Tracking), U.S. Pat. No. 4,739,768. These procedures utilize endovascular guidewires and catheters, introduced quite remotely, to access the aneurysm. Specifically by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable occlusive device which may be introduced to a selected body site using endovascular placement procedures, is found in U.S. Pat. No. 4,994,069, to Ritchart et al. There is described a device—typically a platinum/tungsten alloy coil having a very small diameter—which may be introduced to the selected site through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as found in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

A further variation of the Guglielmi detachable coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

A continuation-in-part application to the Guglielmi et al patent discussed above, U.S. Pat. No. 5,354,295, "IMPROVEMENTS IN AN ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS" issued Oct. 11, 1994, describes the use of mechanically detachable embolic devices as well as those which are electrolytically detachable. The embolic devices may be augmented with attached filaments.

3

Dr. Taki has devised a variation of the Guglielmi detachable coil using a copper link between the guidewire and the coil.

None of these devices utilize a distal portion which is insulated.

SUMMARY OF THE INVENTION

As noted above, this invention is a device used in forming an occlusion at a selected site typically within the human body. In general, the device comprises an elongated body having a proximal end and a distal end. The body length between those ends has a longitudinal axis and typically a lumen running within the elongated body. The elongated body is typically tubular although it need not be. A detachable joint is often found at the proximal end of the elongated body member. Central to this invention is the presence of an insulating region near the distal tip of the body member. The proximal portion and the connective joint are electrically conductive.

The body member itself may be a helically wound coil, tubular braid, or other suitable form for occluding a cavity or lumen within the human body.

The inventive device is typically used in conjunction with a DC source, an AC source, or a modulated RF source in such a way that it either produces an occlusion in the chosen body site or constricts the lumen into which it is placed. The device is often left at the selected site but in some occasions may be removed if such is desired by the attending physician.

DESCRIPTION OF THE INVENTION

Figure 1:
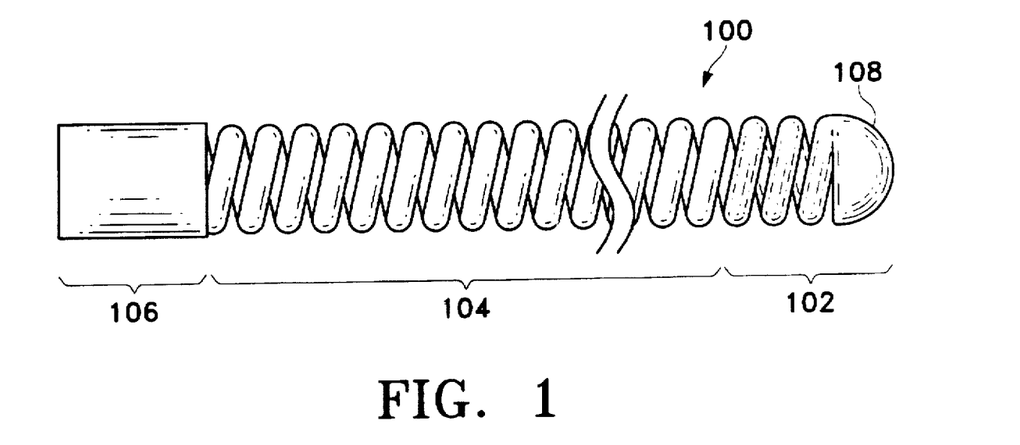
FIG. 1, shows a side view of a typical device made according to this invention showing the conventions used in describing the invention herein.

FIG. 1 provides a side view of a generic representation of the inventive device (100). In this view, three important portions of the device may be seen: the insulated region (102) located distally, the conductive region (104) extending between the insulated region (102) and the connective joint (106), and the connective joint (106) itself. A tip (108) may also be seen and although highly desirable from an operational point of view, is not central to this invention.

As has been discussed above, this invention may be used in conjunction with the procedure discussed in the Guglielmi patents or, more preferably, is used in a similar procedure which involves the imposition of a radio-frequency component to the device. In the earlier described Guglielmi procedures, a DC current is sent through an insulated wire connected to the device. The current is held at a level sufficient to cause a specially designed joint located just proximally of the coil itself to erode thereby allowing the connective wire to be withdrawn. Once the connective wire is withdrawn, the coil forms an embolus at the desired site in the vasculature. Such a site might be, for instance, within an aneurysm. This invention may be used in that variation of the Guglielmi procedure.

The radio-frequency variation of the Guglielmi procedure is described in U.S. patent application Ser. No. 08/499,525 (Attorney Docket 290252013200), the entirety of which is incorporated by reference. In essence, the latter variation desirably involves the imposition of a radio-frequency signal into the device for the specific purpose of causing a spasm in the blood vessel (or other lumen or cavity) and thereby causing a collapse of the vessel wall onto the coil. It is this formation of a region of collapse that distinguishes the later Guglielmi procedure from the earlier method.

The invention described herein is especially useful in the radio-frequency version of the procedure. We have observed that when using the radio-frequency version of the method, that if the distal end of the device is left unprotected (that is to say "uninsulated") that the distal end has a tendency to erode or even to perforate the vessel wall. We found that by insulating the most distal portion of the device causes the current to flow from the device in a way which appears to cause contraction of the vessel site about the conductive portion (104) of the device (100) without causing the noted side-effects. Hence, this invention has three sections. The insulated region (102) is for the purpose of preventing current flow at the distal region of the device (100). The conductive region (104) is for the purpose of allowing current flow along the region into the surrounding tissue. The connective joint (106) is for the purpose of electrically and mechanically connecting the device (100) to a core wire or some other similar component used to place the device (100) at the desired site within the body.

Figure 2:
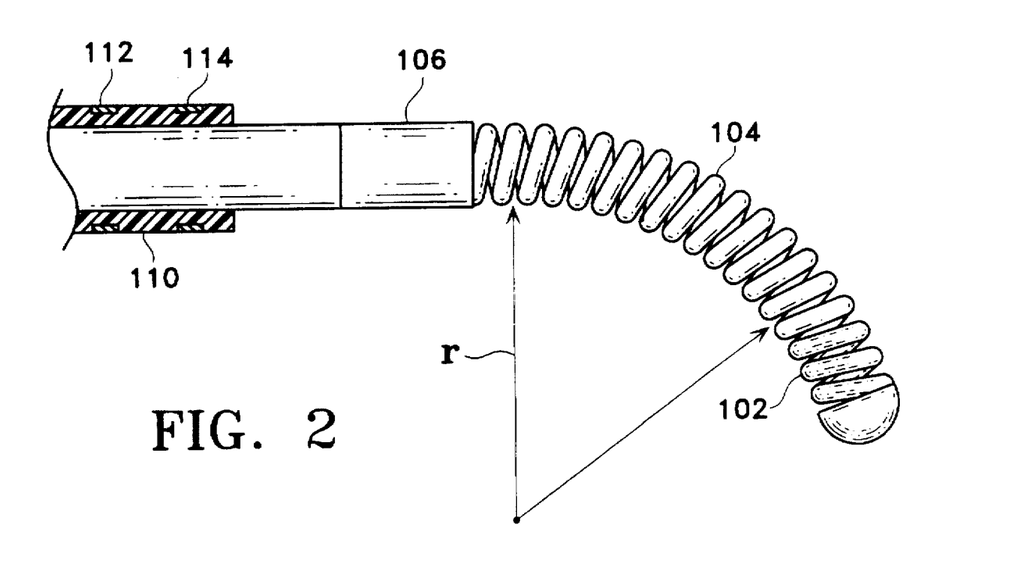
FIG. 2 shows a side view of the inventive device attached to a pusher.

Placement of the device (100) in the body may be achieved by the methods described in a variety of patents, e.g., U.S. Pat. No. 4,994,069, to Ritchart et al. In this approach, a chosen vascular site is entered by use of a catheter such as those shown in Engelson (Catheter Guidewire), U.S. Pat. No. 4,884,575 and also in Engelson (Catheter for Guidewire Tracking), U.S. Pat. No. 4,739,768. These patents describe procedures using guidewires and catheters which allow access to the site from remote portions of the body. Specifically, by the use of catheters having very flexible distal regions and guidewires which are steerable to the region of the aneurysm, embolic devices may be delivered through the catheter to the remote vascular site. The guidewires described in these patents typically have a soft distal tip which may be bent or "formed" by the physician using the device to allow the guidewire to be used to select a path at a junction between vessels. FIG. 2 shows the use of the device (100) as a guidewire tip. The distal-most section of the access catheter (110) and its desired radio-opaque tip markers (112 and 114) may also be seen. The device (100) may be bent to have a radius similar to that of a dime. The radius is not particularly critical but the bend should not approach (or surpass) 90° because of the resulting lack of maneuverability and inability to achieve linearity when the vessel is collapsed during the radio-frequency procedure.

In each of FIGS. 1 and 2, the conductive section (104) and the insulated section are shown to be a helically wound coil. Such a configuration is not required and variations of the physical configuration will be discussed below. The material used in constructing the conductive portions of the device (100), the conductive region (104) and, in certain configurations, the interior portions of the insulated region, may be any of a wide variety of materials; preferably, a radio-opaque material such as a metal or a polymer is used. Suitable metals and alloys for the wire making up those regions include the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biologically inert. Highly preferred is a platinum/tungsten alloy, e.g., 8% tungsten and the remainder platinum.

The wire may also be of any of a number of stainless steels if some sacrifice of radiopacity or flexibility may be tolerated. Very desirable materials of construction, from a mechanical point of view, are materials which maintain their shape despite being subjected to high stress. Certain "superelastic alloys" include nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as a very small diameter wire.

If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radiopaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive member, it is desirably filled with some amount of a known radiopaque material such as powdered tantalum, powdered tungsten, bismuth oxide, barium sulfate, and the like. Obviously, the polymer must be inherently conductive, e.g., certain polyacetylenes or polyanilines, or be doped with a powdered metal or other adjuvant to provide the device (100) with conductivity.

The axial length of the device will usually fall in the range of 0.10 to 100 cm. If used with a radio-frequency version the length is typically 0.25 to 0.75 cm., more preferably about 0.5 cm. If used in other procedures, the length is more usually 2.0 to 40 cm. Depending upon usage, the coil may well have 10–75 turns per centimeter, preferably 10–40 turns per centimeter. Generally speaking, when the device (100) is formed of a metallic coil and that coil is a platinum alloy or a superelastic alloy such as nitinol, the diameter of the wire will be in the range of 0.0005 and 0.006 inches. Wire of such diameter is wound into a primary form diameter of between 0.005 and 0.025 inches. For most neurovascular indications, the preferable device diameter is 0.006 to 0.018 inches. Each of the dimensions are provided only as guidelines and are not critical to the invention. However, only dimensions suitable for use in occluding sites within the human body are included in the scope of this invention.

Figure 3:
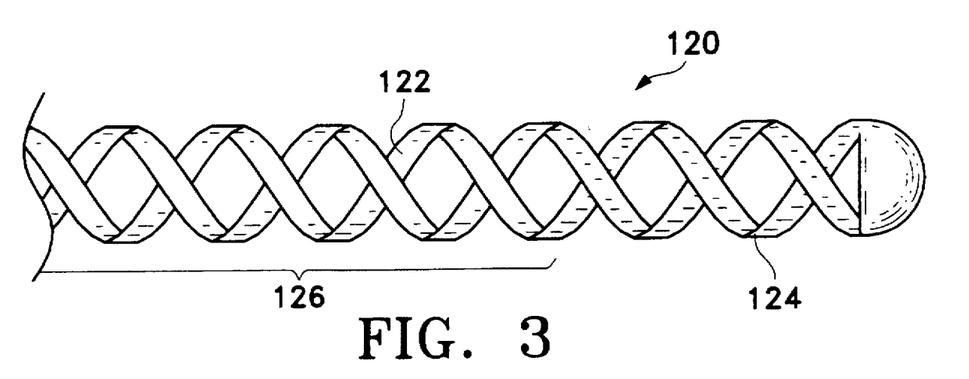
FIG. 3 shows a braided variation of the inventive device.

FIG. 3 shows a variation of the inventive device (120) in which a braided member is used in place of the helical coil shown above in FIGS. 1 and 2. The filamentary elements (122) making up the device (120) may be either a circular in cross-section, e.g., a wire, or may be ribbon-like in configuration. Some overall flexibility is sacrificed in a braided configuration but for the short device (120) as used in the radio-frequency version of the procedure, a braid is acceptable. The insulated region (124) may also be seen.

In each of the configurations discussed above, the insulation is shown as being a coating on a continuation of the conductive sections. The insulation typically is a polymer such as polyethylene, polypropylene, polyurethane, polyethylene terephthalate, polyvinylchloride, or the like and may be applied by a number of procedures. They may be applied by shrink-wrapping the insulators onto the device in the form of tubing. The device may be dipped in molten polymer. The insulation may be sprayed on in the form of a suspension or latex. Each of these procedures and polymers has benefits and detriments, e.g., added stiffness or complicated adjuvant process steps.

One very desirable thermoplastic insulator is generically known as parylene. There are a variety of polymers (e.g., polyxylylene) based on paraxylylene. These polymers are typically placed onto a substrate by vapor phase polymerization of the monomer. Parylene N coatings are produced by vaporization of a di(P-xylylene) dimer, pyrollization, and condensation of the vapor to produce a polymer that is maintained at a comparatively lower temperature. In addition to parylene-N, parylene-C is derived from di(monochloro-P-xylylene) and parylene-D is derived from di(dichloro-P-xylylene). There are a variety of known ways to apply parylene to substrates. Their use in surgical devices has been shown, for instance, in U.S. Pat. No. 5,380,320 (to J. R. Morris), in U.S. Pat. No. 5,174,295 (to Christian et al.), in U.S. Pat. No. 5,067,491 (to Taylor et al.) and the like. A coating of less than about 0.001" is highly desirable, preferably less than about 0.00075", e.g., about 0.0002". A parylene coating has the benefits of being very thin and very flexible. Because it may be applied in a vapor-phase process, the masking of the conductive region (104 in FIG. 1 and 126 in FIG. 3) is easily accomplished during coating of the insulated regions.

Figure 4:
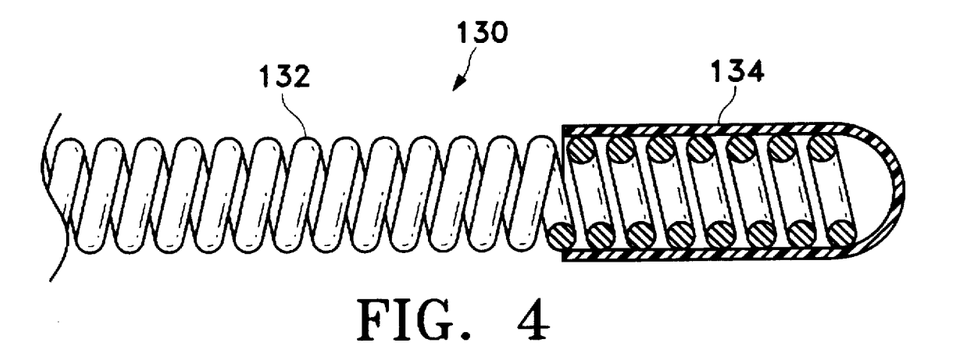
FIG. 4 shows a partial cross section of a capped variation of the inventive device.
Figure 5:
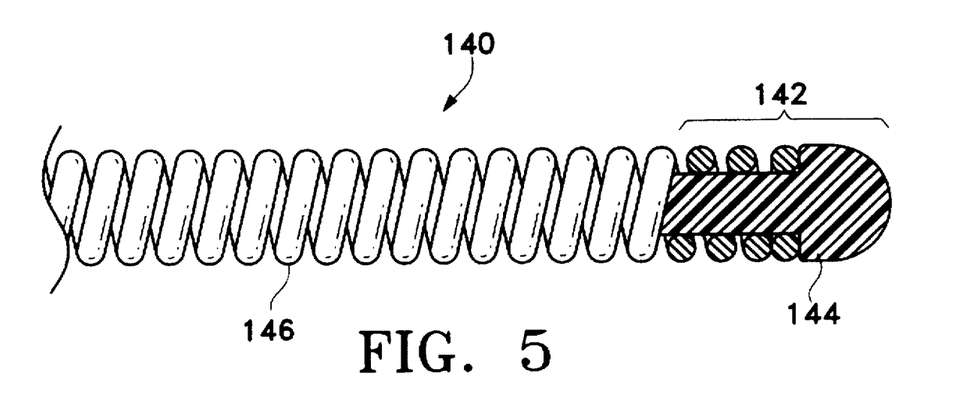
FIG. 5 shows a partial cross sectional side view of the inventive device utilizing using a plugged distal end.

In general, by "insulative", we mean that the insulator has a resistance of 500 kilohms/cm or greater. FIGS. 4 and 5 show variations of the invention in which the wire or ribbon component of the device in not coated, per se, in the insulated region but is either covered with an insulating sleeve or is an insulator itself.

FIG. 4 shows a variation of the inventive device (130) in which the conductive coil (132) is distally covered with a sleeve (134). The sleeve (132) need not be closed at the distal end. Suitable polymers for the sleeve include the polymeric materials discussed above which are of a type that can be shrunk wrapped onto the underlying coil (132) or braid.

FIG. 5 shows a variation (140) of the invention in which the insulated region (142) comprises a plug (144) or insert which is affixed in the distal end of the coil (146) or braid. Again, the material making up the distal tip is insulative and preferably polymeric.

As was mentioned above, the connective joint (106 in FIG. 1) found proximally on the device may be simply a connection which conducts electricity into the conductive region. That is to say that in some treatments using the inventive device, the device is not left in the body after the treatment is completed.

Figure 6:
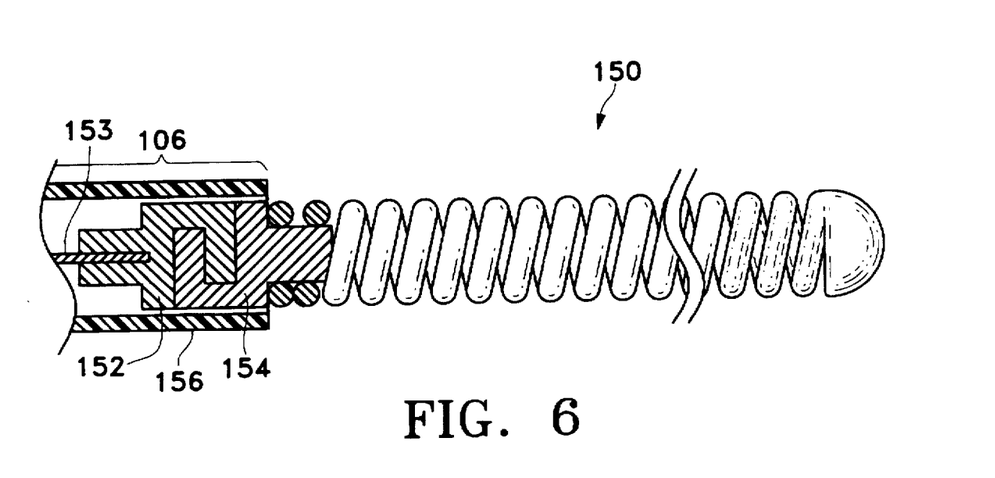
FIG. 6 shows the inventive device in conjunction with a mechanically detachable joint.

FIG. 6 shows a variation (152) of the invention in which the connective joint (106) is mechanically detachable joint.

The depicted joint has a clasp section (152) which remains with the core wire (153) when the sheath (156) is retracted proximally. The other clasp section (154) remains with the device (150) if the device (150) is left in the body. Other mechanically detachable joints suitable for use with the inventive device are described in:

- U.S. Pat. No. 5,234,437, to Sepetka, (shows a method of unscrewing a helically wound coil from a pusher having interlocking surfaces).
- U.S. Pat. No. 5,250,071, to Palermo, (shows an embolic coil assembly using interlocking clasps mounted both on the pusher and on the embolic coil)
- U.S. Pat. No. 5,261,916, to Engelson, (shows a detachable pusher-vaso-occlusive coil assembly having an interlocking ball and keyway-type coupling)
- U.S. Pat. No. 5,304,195, to Twyford et al. (shows a pusher-vaso-occlusive coil assembly having an affixed, proximally extending wire carrying a ball on its proximal end and a pusher having a similar end, which two ends are interlocked and disengage when expelled from the distal tip of the catheter)
- U.S. Pat. No. 5,312,415, to Palermo (also shows a method for discharging numerous coils from a single pusher by use of a guidewire which has a section capable of interconnecting with the interior of the helically wound coil).
- U.S. Pat. No. 5,350,397, to Palermo et al. (shows a pusher having a throat at its distal end and a pusher through its axis. The pusher sheath will hold onto the end of an embolic coil and will then be released upon pushing the axially placed pusher wire against the member found on the proximal end of the vaso-occlusive coil).

The entirety of which are incorporated by notice.

Figure 7:
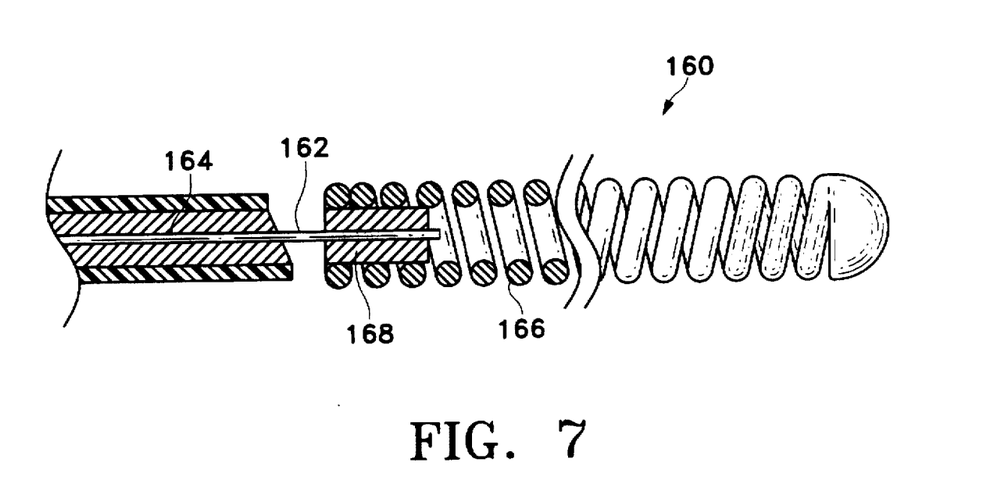
FIG. 7 shows a variation of the device in which the detachable joint is electrolytic in nature.

A further detachable joint is shown in FIG. 7. This joint is described in detail in U.S. Pat. No. 5,423,829, to Pham et al, the entirety of which is incorporated by reference. As incorporated in the inventive device (160) shown in FIG. 7, this joint 162) is one which, upon application of a suitable voltage to the core wire (164) will erode in the bloodstream to allow the device (160) to remain in the body. In this variation, the conductive region (166) is necessarily more "noble" in the electromotive series than the material found in the joint (162). A return electrode (not shown) must be supplied to complete the circuit. Presumably, the erosion of the joint (162) operates through an electrolysis/oxidation of the metal in the joint. The region of the core wire proximal of the joint (162) is insulated to centralize the erosion reaction at the joint. The bushing (168) shown in the FIG. 7 is conductive. Other electrolytic joints suitable for use in this invention are described in the Guglielmi patents described above as well as in Pham et al, the entirety of which are incorporated by reference.

Figure 8:
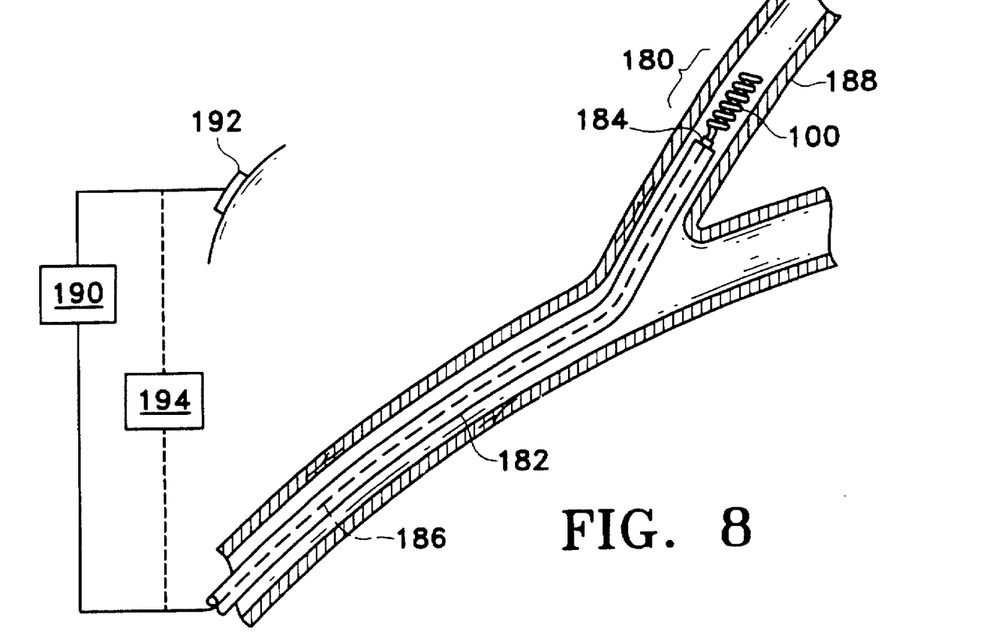
FIGS. 8 and 9 show a typical method of deploying this device.
Figure 9:
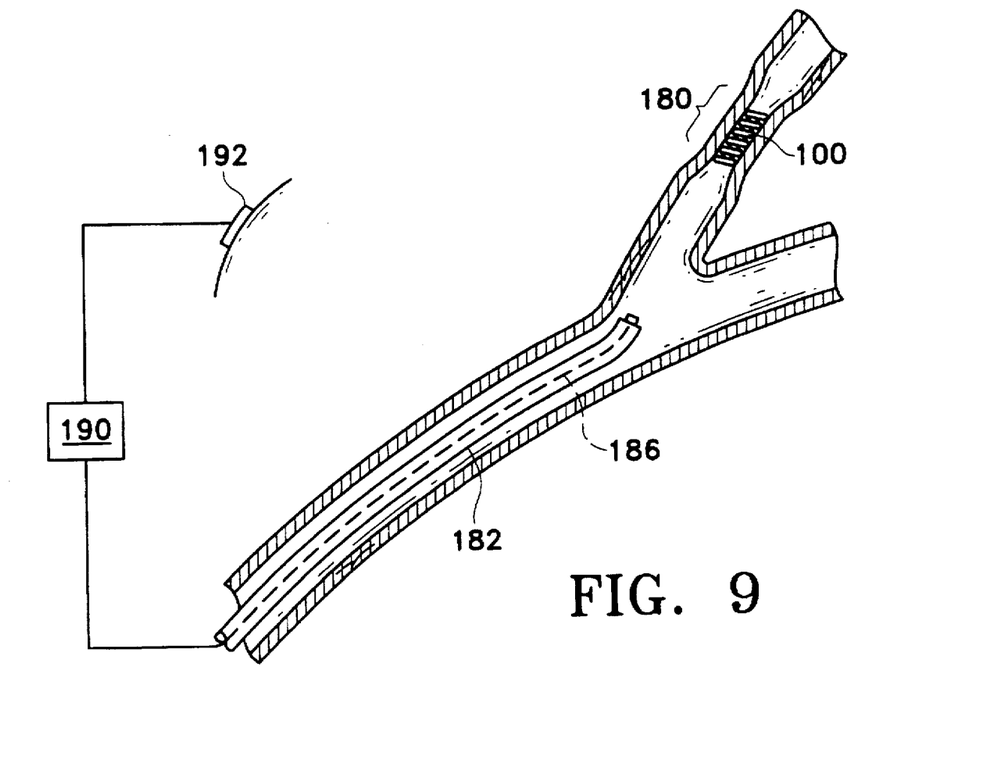

Finally, FIGS. 8 and 9 show the preferred procedure for using the device of the present invention. These Figures summarily depict the radio-frequency variation of the Guglielmi procedure as described in U.S. patent applications Ser. No. 08/499,525 (Attorney Docket 290252013200), the entirety of which is again incorporated by reference.

FIG. 8 shows a site to be occluded (180). A catheter (182) is inserted into the vasculature so that the distal end of the catheter (184) is located at the selected occlusion site (180). The inventive occlusive device (100) is has been passed through and ejected from the distal end (184) of the catheter (182) using delivery or core wire (186). The inventive device is positioned so that it contacts a portion of the vessel wall (188). This positioning may be verified by conventional fluoroscopy. The core wire (186) is connected to an LF or RF generator and thence to the inventive occlusion device (100). The other pole of the RF generator (190) is connected to a dispersive electrode (192) which preferably is in the form of a large conductive pad. An alternating signal (e.g., 10 Hz. to 10 Mhz.) signal imposed on the coil/. A 4 Mhz. is especially preferred. The signal to the device (100) heats the selected vascular site (180) and constricts the wall of that vessel (180) as is shown in FIG. 9. In the depicted variation, an electrolytically detachable of about 0.018" outside diameter and 0.5 cm. is deployed. The occlusion is verified most preferably by the use of a reflected power monitoring device (194) which is used as discussed in the manner described in U.S. patent application Ser. No. 08/499,525 (Attorney Docket 290252013200).

In this variation of the invention, the occlusive device (100) is then severed from the core wire (186) by use of the electrolytic procedure and voltage source (198) described in the Guglielmi patents mentioned above. Catheter (186) is then withdrawn from the body.

The illustrated embodiments have been used only for the purposes of clarity and should not be taken as limiting the invention as defined by the following claims.

We claim as out invention:

1. An occluding device comprising an elongated body member having a proximal end and a distal end and a body length between said proximal and distal ends, a detachable joint attached to said body member proximal end capable of conducting an electrical current through said joint to said body member, wherein said body member is comprised of at least a proximal conductive region comprising a conductive material and a distal insulated region having a length between about 5 and 25% of the body length wherein said distal insulated region is insulated with a polyxylylene polymer.

2. The device of claim 1 wherein said body member comprises a helically wound coil.

3. The device of claim 1 wherein said body member comprises a tubular braid.

4. The device of claim 1 wherein said distal insulated region comprises an insulator comprising a polyxylylene polymer.

5. The device of claim 1 wherein said distal insulated region comprises a core of a conductive material and an insulating covering comprising a polyxylylene polymer.

6. An occluding device comprising an elongated tubular braided body member having a proximal end and a distal end and a body length between said proximal and distal ends, a detachable joint attached to said body member proximal end capable of conducting an electrical current through said joint to said body member, wherein said body member is comprised of at least a proximal conductive region comprising a conductive material and a distal insulated region having a length between about 5 and 25% of the body length.

7. The device of claim 6 wherein said distal insulated region comprises an insulator.

8. The device of claim 6 wherein said distal insulated region comprises an insulator.

9. The device of claim 6 wherein said distal insulated region comprises a core of a conductive material and an insulating covering.

10. The device of claim 6 wherein the distal insulated region is insulated with a polyxylylene polymer.

* * * * *

UNITED STATES PATENT AND TRADEMARK OFFICE

CERTIFICATE OF CORRECTION

PATENT NO. : 5,743,905

DATED : April 28, 1998

INVENTOR(S) : Joseph Eder, Guido Guglielmi and Cheng Ji

It is certified that error appears in the above-identified patent and that said Letters Patent is hereby corrected as shown below:

Column 6, line 50, replace "(132)" with --(134)--;

Column 6, line 66, replace "(152)" with --(150)--;

Column 8, line 11, before the word "detachable" insert --section of device (100)--;

Column 8, line 19, replace "(198)" with --(190)--.

Signed and Sealed this

Twenty-fifth Day of May, 1999

*Attest:*

Q. TODD DICKINSON

*Attesting Officer*       *Acting Commissioner of Patents and Trademarks*